US012168715B2

(12) United States Patent
Chaturvedi

(10) Patent No.: US 12,168,715 B2
(45) Date of Patent: Dec. 17, 2024

(54) PROCESS OF MANUFACTURING BIODEGRADABLE PET CHIPS

(71) Applicant: Ashok Chaturvedi, New Delhi (IN)

(72) Inventor: Ashok Chaturvedi, New Delhi (IN)

( * ) Notice: Subject to any disclaimer, the term of this patent is extended or adjusted under 35 U.S.C. 154(b) by 449 days.

(21) Appl. No.: 17/441,015

(22) PCT Filed: Mar. 13, 2020

(86) PCT No.: PCT/IN2020/050230
§ 371 (c)(1),
(2) Date: Sep. 20, 2021

(87) PCT Pub. No.: WO2020/188594
PCT Pub. Date: Sep. 24, 2020

(65) Prior Publication Data
US 2022/0153926 A1    May 19, 2022

(30) Foreign Application Priority Data

Mar. 20, 2019   (IN) .............................. 201911010930

(51) Int. Cl.
| | |
|---|---|
| *C08G 63/183* | (2006.01) |
| *B01J 8/24* | (2006.01) |
| *B29B 9/06* | (2006.01) |
| *B29K 67/00* | (2006.01) |
| *C08G 63/78* | (2006.01) |
| *C08G 63/85* | (2006.01) |
| *C08G 63/86* | (2006.01) |
| *C12P 7/625* | (2022.01) |

(52) U.S. Cl.
CPC .............. *C08G 63/183* (2013.01); *B01J 8/24* (2013.01); *B29B 9/065* (2013.01); *C08G 63/785* (2013.01); *C08G 63/85* (2013.01); *C08G 63/866* (2013.01); *C12P 7/625* (2013.01); *B29K 2067/003* (2013.01); *B29K 2995/006* (2013.01); *C08G 2230/00* (2013.01)

(58) Field of Classification Search
CPC .......... C12P 7/625; C08L 67/02; C08L 89/00; C08G 2230/00; C08G 63/183; C08G 63/78; C08G 63/785; C08G 63/85; C08G 63/866; Y02W 30/62
See application file for complete search history.

(56) References Cited

U.S. PATENT DOCUMENTS

| 9,925,707 B2* | 3/2018 | Iyer ....................... B29C 48/022 |
| 2006/0173154 A1* | 8/2006 | Charbonneau ......... C08K 5/005 |
| | | 528/272 |
| 2008/0194771 A1* | 8/2008 | Kong ........................ C08F 2/24 |
| | | 435/135 |
| 2009/0131627 A1* | 5/2009 | Colhoun ............... B29C 48/832 |
| | | 528/308 |
| 2012/0136132 A1* | 5/2012 | Schulz Van Endert ..................... B01J 19/247 |
| | | 528/308.8 |
| 2014/0197580 A1* | 7/2014 | Poulat .................. C08G 63/183 |
| | | 528/307 |

FOREIGN PATENT DOCUMENTS

JP    H06322263    * 11/1994
WO    2013034743 A1    3/2013

OTHER PUBLICATIONS

Yi Jiang et al "Enzymatic Synthesis of Biobased Polyesters Using 2,5-Bis(hydroxymethyl)furan as the Building Block", Biomacromolecules 2014, 15, 2482-2493 (Year: 2014).*
Hiroshi Uyamaet al "Enzymatic Synthesis of Aromatic Polyesters by Lipase-Catalyzed Polymerization of Dicarboxylic Acid Divinyl Esters and Glycols", Polymer Journal, vol. 31, No. 4, pp. 380-383 (1999) (Year: 1999).*
TH. Rieckmann et al "Poly(Ethylene Terephthalate) Polymerization—Mechanism, Catalysis, Kinetics, Mass Transfer and Reactor Design", Modern Polyesters: Chemistry and Technology of Polyesters and Copolyesters, 2003 (Year: 2003).*
Alessandro Pellis et al "Fully renewable polyesters via poly-502condensation catalyzed by Thermobifida cellulosilytica cutinase 1: an integrated approach", Green Chem., 2017, 19,pp. 490 (Year: 2017).*
A. Pellis et al "Enlarging the tools for efficient enzymatic polycondensation: structural and catalytic features of cutinase 1 from Thermobifida cellulosilytica" (Year: 2016).*
Yoshida et al "A bacterium that degrades and assimilates poly( ethylene terephthalate)", Science 2016, vol. 351 Isue 6278, pp. 1196-1199 (Year: 2016).*
Shiro Kobayashi "Review—Lipase-catalyzed polyester synthesis—A green polymer chemistry", Proc. Jpn. Acad., Ser. B 86 (2010) (Year: 2010).*
W.Goltner "Solid-State Polycondensation of Polyester Resins: Fundamentals and Industrial Production", Modern polyesters, Chapter 5. (Year: 2003).*
Ronkvist et al "Cutinase-Catalyzed Hydrolysis of Poly(ethylene terephthalate)", Macromolecules 2009, 42, 5128-5138 (Year: 2009).*

(Continued)

*Primary Examiner* — Frances Tischler
*Assistant Examiner* — Gennadiy Mesh
(74) *Attorney, Agent, or Firm* — Dinsmore & Shohl LLP

(57) ABSTRACT

The present invention describes a process of manufacturing biodegradable PET chips, comprising the steps of providing a purified terephthalic acid (PTA) in a predetermined quantity in a slurry tank; providing virgin monoethylene glycol (MEG) in a predetermined quantity in the slurry tank; transferring the combination of the slurry tank to an esterification reactor for esterification of the combination in the reactor at above 250° C. temperature which releases monomers; transferring the monomers from the esterification reactor to a polymerisation reactor; providing poly-catalysts such as, but not limited, to Ti-based catalyst, sb2O3 or any other suitable catalysts or combination thereof into the polymerisation reactor; and polymerization of the monomers in the polymerisation reactor at above 280° C. temperature, wherein an enzyme based composition is provided either at PTA/MEG stage or poly-catalyst stage or at other stages or combination thereof.

17 Claims, 4 Drawing Sheets

(56) References Cited

OTHER PUBLICATIONS

International Search Report and Written opinion dated Sep. 30, 2020 pertaining to PCT Application No. PCT/IN2020/050230 filed Mar. 13, 2020.

\* cited by examiner

PROCESS OF MANUFACTURING BIODEGRADABLE PET CHIPS

CROSS-REFERENCES TO RELATED APPLICATIONS

This application is a national-stage application under 35 U.S.C. § 371 of International Application No. PCT/IN2020/050230, filed Mar. 13, 2020, which international application claims the benefit of priority to Indian Patent Application No. 201911010930, filed Mar. 20, 2019.

FIELD OF THE INVENTION

The present invention relates generally to biodegradable PET polymeric raw material. In particular, the present invention relates to a process of manufacturing biodegradable polyethylene terephthalate or PET chips for use in making biodegradable polyester package such as film/laminate pouches, bottles, trays or any other product.

BACKGROUND

Plastics are typically organic polymers of high molecular mass. They are usually synthetic and made by polymerisation, most commonly derived from petrochemicals. Plastics are inexpensive, durable and easy to process substances compared to the other options, which are employed to manufacture a variety of components that find usage in a wide range of applications. As a consequence, the production of plastics has increased dramatically over the last few decades. For example, polyethylene terephthalate, or PET, is a widely produced thermoplastic polymer for manufacturing polymeric products such as films, bottle etc. Because of the durability of the polymeric products having high resistance to degradation (due to high molecular mass values, hydrophobicity and crystallinity), despite being recyclable, due to poor collection, substantial quantities of disposable plastics are piling up in landfill sites and in natural habitats, generating increasing environmental problems worldwide.

To answer these problems, different physical, chemical and/or biochemical approaches have been developed to reduce the biodegradation resistance of polymeric products and to increase their biodegradation rate. For example, additives have been introduced to mix/blend with non-biodegradable polymeric resins during user end polymeric product manufacturing stage to make polymeric product biodegradable. However the mixing of additives during the end product manufacturing to make biodegradable polymeric product appears to be satisfactory, but mixing of additive during end product manufacturing, particularly for large scale production for packaging and other products made of polyester or PET chips having specific properties including a minimum intrinsic viscosity and uniform dispersion, requires additional complex observation, expertise, testing and quality control. This inhibits the adaptation of the process of mixing the additive at end product manufacturing stage to make biodegradable product.

Thus, there is a need of biodegradable PET chips for making biodegradable PET polymeric products, ready to use for making bio degradable polymeric products without mixing of such additive at the end product manufacturing stage.

SUMMARY OF THE INVENTION

The present invention describes a process of manufacturing biodegradable PET chips, comprising the steps of providing a purified terephthalic acid (PTA) in a predetermined quantity in a slurry tank; providing virgin and/or recycled Mono-Ethylene Glycol (MEG) in a predetermined quantity in the slurry tank; transferring the combination of the slurry tank to an esterification reactor for esterification of the combination in the reactor at above 250° C. temperature which releases monomers; transferring the monomers from the esterification reactor to a polymerisation reactor; providing poly-catalysts such as, but not limited, to Ti-based catalyst, $Sb_2O_3$ or any other suitable catalysts or combination thereof into the polymerisation reactor; and polymerization of the monomers in the polymerisation reactor at above 280° C. temperature, wherein an enzyme based composition is provided either at PTA/MEG stage or poly-catalyst stage or at other stages or combination thereof.

DETAILED DESCRIPTION OF THE PRESENTLY PREFERRED EMBODIMENTS

While the present invention has been described in connection with what are currently considered to be the most practical and preferred embodiments, it is to be understood that various arrangements and alternative embodiments are intended to be included within the scope of the appended claims.

The present invention generally describes a biodegradable PET polymeric raw material and more particularly a process of manufacturing film grade biodegradable polyethylene terephthalate or PET chips for use in making biodegradable polyester film/laminate package. The biodegradability in the PET chips is induced by an enzyme based composition, present either on the surface or in the entire thickness of the chips, provided at one of the steps or combination thereof, of the process.

The enzyme in the enzyme-based composition are natural protein molecules that act as highly efficient catalysts in biochemical reactions, that is, they help a chemical reaction take place quickly and efficiently. Studies show that the enzymes present in the enzyme-based composition attracts microbes over the polymeric product surface and colonize on the surface of the plastic forming a biofilm and thus accumulating the microbes on the polymeric product surface. Once the microbes have colonized on the product surface they secrete acids and/or enzymes that break down the polymeric chains. The microbes utilize biodegradable polymeric as the component in unavailability of microbial nutrients.

The formulation of the enzyme based composition may include, but not limited to, natural peptides/enzymes/proteins obtained from edible biological sources such as plant or vegetables etc.

Typical enzyme-based compositions are described in Indian patent Appl. Nos. 3104/MUM/2015 and 201611028054, and U.S. Pat. No. 9,925,707/EP3162841, however any other similar/modified composition can also be used without deviating from the scope of the present invention.

With reference to FIGS. 1, 2, 3 and 4, various embodiments of the present invention will now be described.

Figure 1:
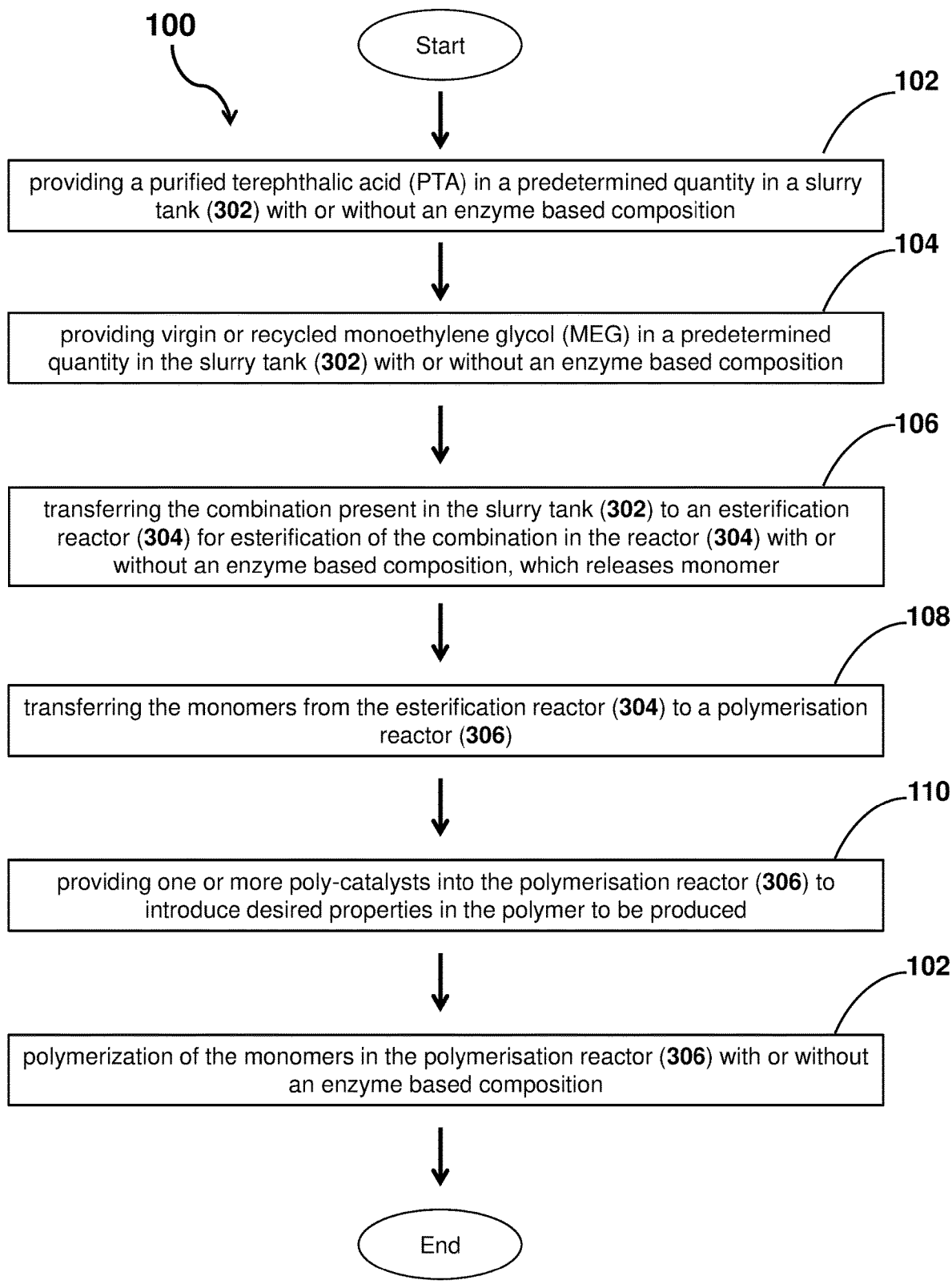
FIG. 1 depicts a flow chart of a process (100) for production of film grade biodegradable polyethylene terephthalate chips, in accordance with an embodiment of the present invention.

FIG. 1 depicts a flow chart of a process (100) for production of biodegradable polyethylene terephthalate chips, in accordance to an embodiment of the present invention.

The process (100) of manufacturing biodegradable PET chips includes step (102) of providing a purified terephthalic acid (PTA) in a predetermined quantity in a slurry tank (302). The predetermined quantity of the PTA may be 68% by weight; however other suitable quantity of the PTA may be provided based on requirement without deviating from the scope of the present invention. The process (100) further includes the step (104) of providing virgin or recycled Mono-Ethylene Glycol (MEG) in a predetermined quantity in the slurry tank (302). The predetermined quantity of the MEG is typically 31% by weight; however other suitable quantity of the MEG may be provided based on requirement without deviating from the scope of the present invention. The process (100) further includes the step (106) of transferring the combination of the slurry tank (302) to an esterification reactor (304) for esterification of the combination in the reactor (304) which releases monomer. The esterification happens in the esterification reactor (304) at temperature range of above 250° C. under 2.5 bar pressure releasing the monomers and water vapours. At step (106), the esterification success is confirmed if 95% by weight measured quantity of distilled water, obtained from the water vapour, is extracted from the esterification reactor (304).

The process (100) further includes the step (108) of transferring the monomers from the esterification reactor (304) to a polymerisation reactor (306). The polymerization reactor (306) may have a capacity of 20 m$^3$; however reactor (306) of other capacity may also be used without deviating from the scope of the present invention. The process (100) further includes the step (110) of providing poly-catalysts into the polymerisation reactor (306) to induce desired properties in the polymer to be produced. The poly-catalysts may be, but not limited to, Ti-based catalyst, $Sb_2O_3$ or any other suitable catalysts known in the art or combination thereof. The process (100) further includes the step (112) of polymerization of the monomers in the polymerisation reactor (306). The polymerization of the monomers occur by retaining the monomers in the reactor (306) for a period of 1.5-3 hours having vacuum environment at the temperature range of above 280° C.

At step (112) of the process (100), the polymerization of the monomers take place in the polymerization reactor (306) at the above mentioned predetermined temperature range producing PET polymers. The produced PET polymers (polymerized monomers) are pushed by a pressure of inert gases such as Nitrogen ($N_2$) from top of the polymerisation reactor (306) to push through strands die (308), of a suitable specification, configured to the polymerization reactor (306). In an example, specification of the strands die (308) includes a plurality of holes, such as but not limited to 95 number of holes, each having diameter of size approx. 8 mm, however strands die (308) of different specification may also be used without departing from the scope of the present invention. The strands coming out of the die (308) are stretched up to a predetermined length, such as but not limited to 1.5 meters. The stretched strands are cooled inline by spraying chilled demineralization (DM) water over the stretched strands or by other suitable cooling mechanism such as but not limited to automatic strand in-feed underwater. The cooled PET polymer strands are thereafter pelletized in chips of a predetermined shape, such as but not limited to 4×4×3 mm inline using roller pelletizer or other suitable pelletizer.

The enzyme based composition, as discussed heretofore above, is provided either with PTA at (102) or with MEG at (104) or poly-catalyst stage (110) or at other stages or combination thereof in order to induce biodegradability in the polymeric chips to be produced by using the process (100).

The biodegradable PET chips may also be produced by providing the enzyme based composition at any of the steps or combination thereof, of the above described process (100) of manufacturing the PET chips if the composition is water insoluble. In other case, the composition can be provided only at the stages/steps or combination thereof, except the step of esterification, for producing biodegradable PET chips.

The biodegradable PET chips may also be produced by providing the aqueous enzyme-based composition in the cooling water of the underwater palletizer and then cutting the strands to chips. The dried chips have a coating of the enzyme-based composition on the surface of chips.

The biodegradable PET chips may also be produced by placing an additional mixing zone to the process (100) for feeding and mixing the enzyme-based composition before pushing the molten phase PET polymer into the strands die (308) and then cooling and cutting the strands to chips having dispersed enzyme-based composition.

The pelletized biodegradable PET chips is transferred to a dryer (310) to evaporate the water from the PET chips before packing up for further usage, such as making polymeric films.

As used herein, PET polymer of textile or fiber grade, film grade, and bottle grade intend to describe PET, which can be described as having an intrinsic viscosity within the range of 0.64-0.75, 0.6-0.66, and 0.57-0.64, respectively. In order to suit the use of the PET polymer of the different grades, it is desirable that the PET have specifications according to following.

| PET grade | Intrinsic Viscosity (IV) |
|---|---|
| Film | 0.6~0.66 |
| Bottle | 0.57~0.64 |
| Fibre/extile | 0.64~0.75 |

Figure 2:
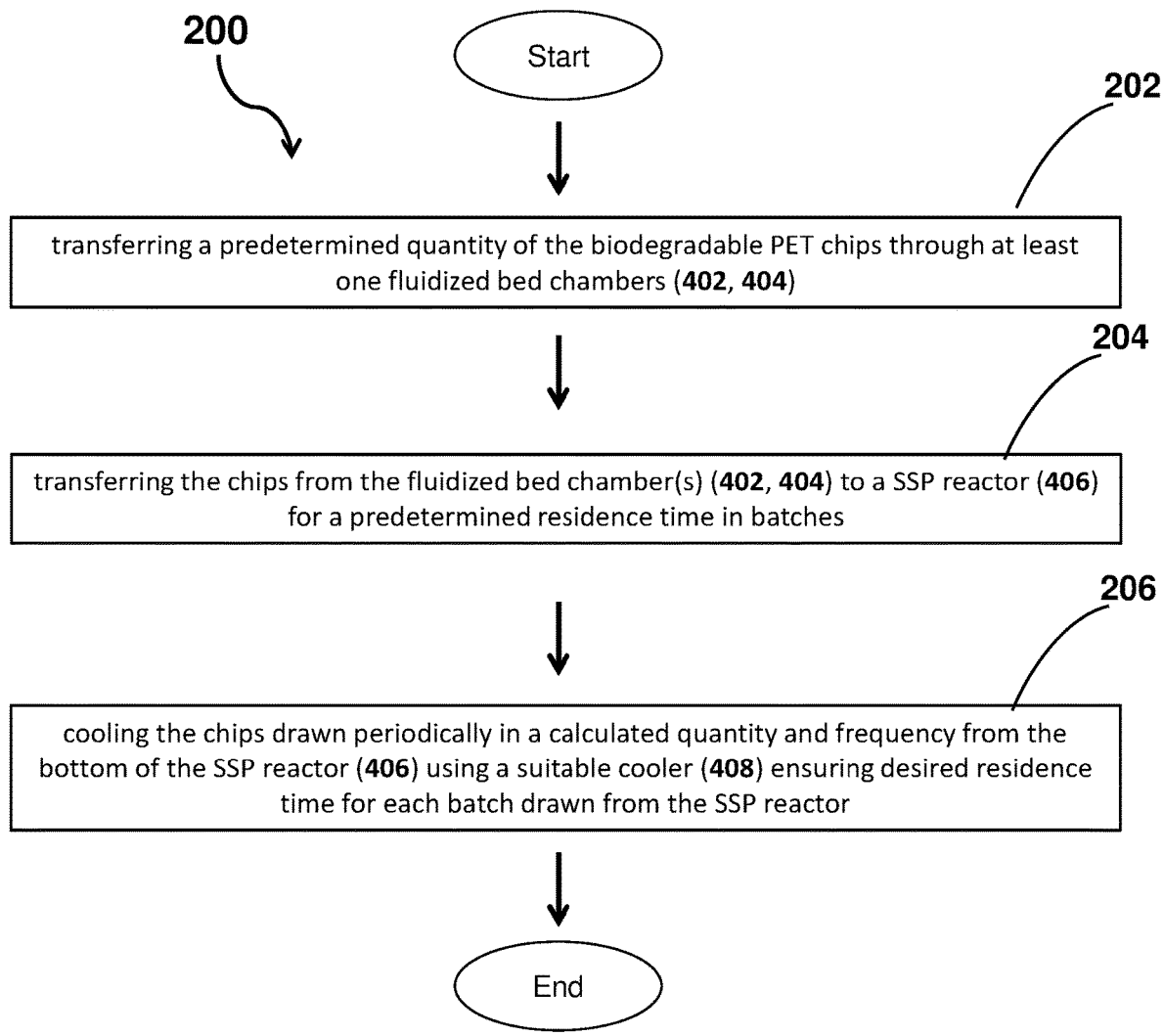
FIG. 2 depicts a flow chart of a process (200) for production of injection moulding and bottle grade biodegradable polyethylene terephthalate chips, in accordance with an embodiment of the present invention.
Figure 3:
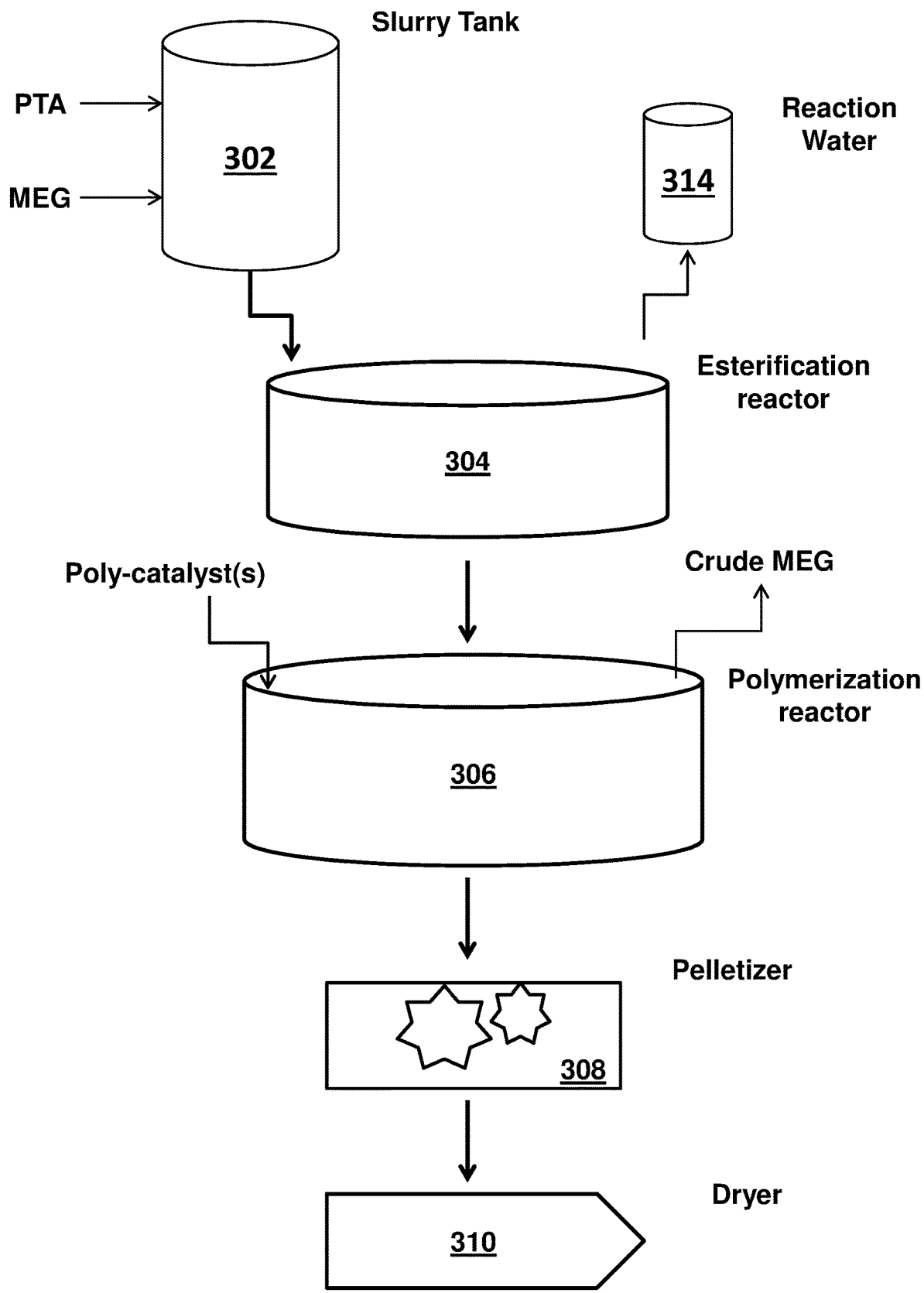
FIG. 3 depicts a schematic illustration of a process (100) for production of biodegradable polyethylene terephthalate chips, in accordance with an embodiment of the present invention.
Figure 4:
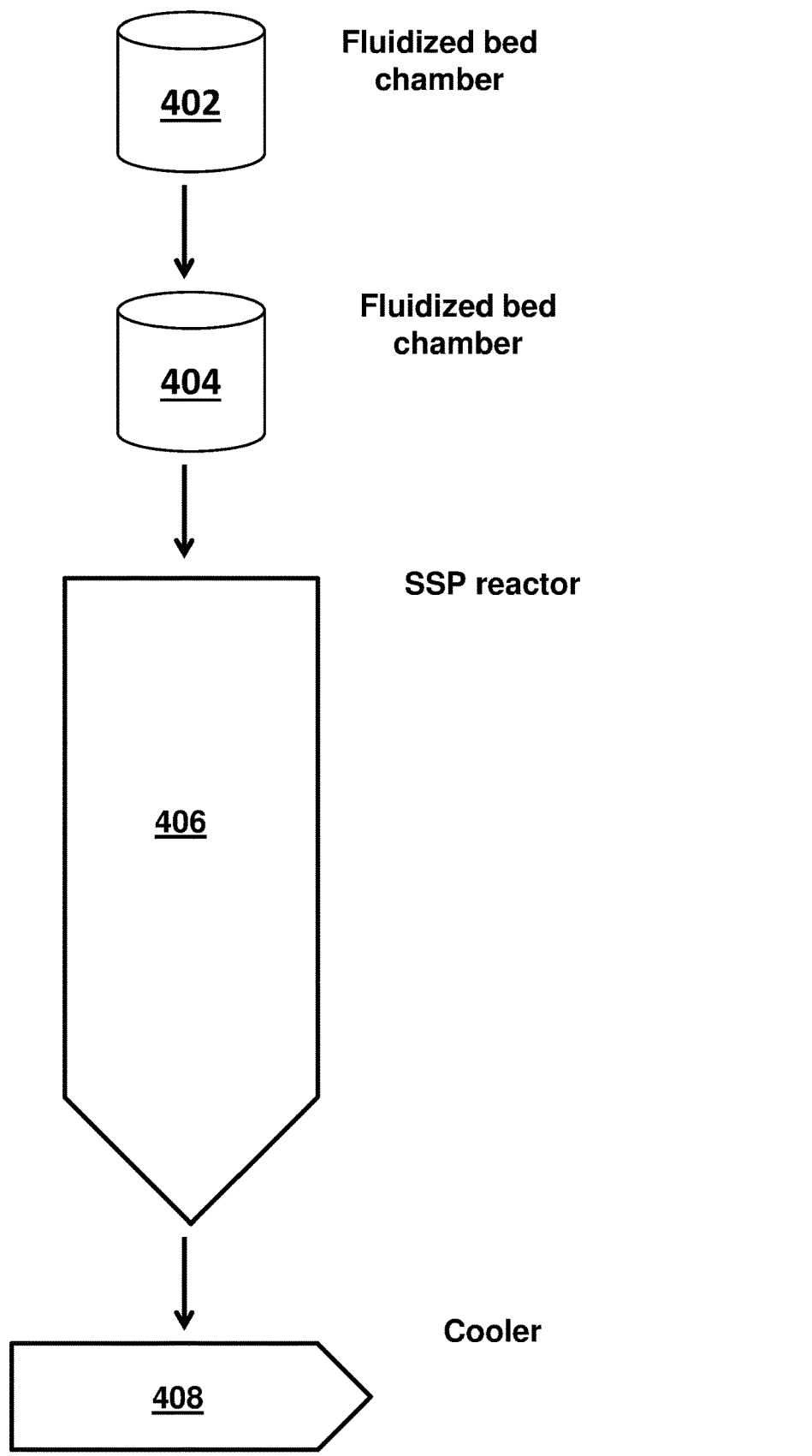
FIG. 4 depicts a schematic illustration of a process (200) for production of biodegradable polyethylene terephthalate chips, in accordance with an embodiment of the present invention.

The above described process (100) produces film grade biodegradable PET chips having IV of 0.6 to 0.66 which can used to make PET polymeric film laminate for various suitable packaging applications. The injection moulding and bottle grade biodegradable PET chips are manufactured using a process (200) as depicted in FIG. 2, according to an embodiment of the present invention, known as Solid State Poly-condensation (SSP) inline to the above described process (100) after the step of pelletizing of the above mentioned process (100), to increase the I.V. (Intrinsic viscosity) suitable for injection moulding, blow moulding, extrusion etc.

The process (200) includes the step (202) of transferring a predetermined quantity of the biodegradable PET chips at a predetermined frequency through at least one pre-crystallizer or crystallizer fluidized bed chambers (402, 404). In an example, the predetermined quantity of the biodegradable chips may be transferred at the rate of 1.5 T/hr., however any other quantity or frequency may also be used without deviating from the scope of the present invention. In the fluidized bed chambers (402, 404), air or Nitrogen gas at 150° C.-170° C. is used to heat the PET chips before transferring to the SSP reactor (406), as described in the next step (204).

The process (200) further includes the step (204) of transferring the chips from the fluidized bed chamber(s) (402, 404) to a SSP reactor (406) of a predetermined capacity for a predetermined residence time in batches.

In an example, the capacity of the SSP reactor (406) is 30 Tons however SSP reactor (406) of other suitable capacity may also be used. In an example, the residence time of the SSP reactor (406) may be in the range of 10-20 hours however the residence time may vary according to the desired IV of the PET chips to be produced.

During the residence in the SSP reactor (406), one or more bi-products such as but not limited to aldehyde, MEG etc. are released which needs to be extracted during the residence time, out of the SSP reactor (406). Inert gas such as Nitrogen (N2) from the bottom of the SSP reactor (406) at 180° C.-200° C. is passed into the SSP reactor (406) in order to extract the bi-products leaving only the biodegradable injection mounding and bottle grade PET chips having the desired IV.

The process (200) further includes the step (206) of cooling the chips, drawn periodically in a calculated quantity and frequency from the bottom of the SSP reactor (406), using a suitable cooler (408) ensuring desired residence time for each batch drawn from the SSP reactor (406).

The biodegradable injection mounding and bottle grade PET chips produced are thereafter ready to be packed up for further usage, such as making polymeric bottle or other suitable products.

For only bottle grade biodegradable PET chips, at step (102) of the process (100) of manufacturing film grade biodegradable PET chips, a predetermined quantity of Purified Isophthalic Acid (IPA) is provided along with PTA making combined weight of IPA and PTA about 68%. The predetermined quantity of the IPA may be 2% by weight and PTA may be 66% by weight making combined quantity 68% by weight; however other suitable quantity of the IPA and PTA may be provided based on requirement without deviating from the scope of the present invention.

In various other embodiments besides or without having addition of enzyme-based composition in afore described stages, the ingredients such as but not limited to PTA, MEG, Polycatalyst etc. may be premixed with at least one of the ingredients in predetermined quantity of enzyme-based composition.

While the present invention has been described in connection with what are currently considered to be the most practical and preferred embodiments, it is to be understood that various arrangements and alternative embodiments are intended to be included within the scope of the appended claims.

I claim:
1. A process of manufacturing biodegradable polyethylene terephthalate (PET), the process comprising:
   (a) providing purified terephthalic acid (PTA) in a slurry tank;
   (b) providing virgin or recycled monoethylene glycol (MEG) in the slurry tank, thereby forming a combination of PTA and MEG in the slurry tank;
   (c) transferring the combination of PTA and MEG from the slurry tank to an esterification reactor;
   (d) esterifying the combination of PTA and MEG in the esterification reactor, thereby forming monomers;
   (e) transferring the monomers from the esterification reactor to a polymerization reactor; and
   (f) polymerizing the monomers in the polymerization reactor, thereby producing PET polymer, wherein one or more poly-catalysts provided in the polymerization reactor comprises at least one of Ti-based catalyst or $Sb_2O_3$,
wherein an enzyme-based composition is provided in one or more of:
   (I) the slurry tank at (a) or (b);
   (II) the esterification reactor at (d), provided the enzyme-based composition is water soluble; or
   (III) the polymerization reactor at (f).
2. The process of manufacturing biodegradable PET according to claim 1, wherein the PTA makes up about 68% by weight of the combination of PTA and MEG.
3. The process of manufacturing biodegradable PET according to claim 1, wherein the MEG makes up about 31% by weight of the combination of PTA and MEG.
4. The process of manufacturing biodegradable PET according to claim 1, wherein the PET polymer produced by polymerization is pushed through a strands die by a pressure of inert gas.
5. The process of manufacturing biodegradable PET according to claim 4, wherein the inert gas is Nitrogen ($N_2$).
6. The process of manufacturing biodegradable PET according to claim 4, further comprising:
   creating strands of PET polymer from the PET polymer pushed through the strands die; and
   stretching the strands of PET polymer to a predetermined length.
7. The process of manufacturing biodegradable PET according to claim 6, wherein the predetermined length of the strands is 1.5 meters.
8. The process of manufacturing biodegradable PET according to claim 6, wherein the stretched strands of PET polymer are cooled inline by spraying chilled demineralized (DM) water over the stretched strands of PET polymer or by feeding the stretched strands into water.
9. The process of manufacturing biodegradable PET according to claim 8, wherein the strands of PET polymer are cooled inline by feeding the stretched strands into water.
10. The process of manufacturing biodegradable PET according to claim 6, wherein the stretched strands of PET polymer are cooled and thereafter pelletized inline into PET chips using a roller pelletizer or an underwater pelletizer.
11. The process of manufacturing biodegradable PET according to claim 6, wherein:
   the stretched strands of PET polymer are cooled and thereafter pelletized inline into PET chips using an underwater pelletizer; and
   the enzyme-based composition is further provided in cooling water of the underwater pelletizer.
12. The process of manufacturing biodegradable PET according to claim 10, wherein prior to pushing the PET polymer through the strands die, the PET polymer is transferred to a mixing zone and mixed with the enzyme-based composition.

13. The process of manufacturing biodegradable PET according to claim 8, wherein the cooled strands of PET polymer are pelletized inline into PET chips using a pelletizer, and wherein the PET chips are transferred to a dryer to evaporate water from the PET chips before packing up for further usage.

14. The process of manufacturing biodegradable PET according to claim 10, further comprising:
   (g) transferring a predetermined quantity of the PET chips at a predetermined frequency through at least one fluidized bed chamber comprising a pre-crystallizer fluidized bed chamber, a crystallizer fluidized bed chamber, or both, to increase the I.V. (Intrinsic viscosity) of the PET chips;
   (h) transferring the PET chips in batches from the at least one fluidized bed chamber to a solid state poly-condensation (SSP) reactor for a predetermined residence time;
   (i) drawing a calculated quantity of the PET chips from a bottom of the SSP reactor; and
   (j) cooling the PET chips drawn from the bottom of the SSP reactor.

15. The process of manufacturing biodegradable PET according to claim 14, further comprising providing Purified Isopthalic Acid (IPA) in the slurry tank along with the PTA in (a) such that the combination of PTA and MEG formed in (b) further comprises IPA.

16. The process of manufacturing biodegradable PET according to claim 15, wherein the IPA makes up 2% by weight of the combination of PTA, IPA, and MEG.

17. The process of manufacturing biodegradable PET according to claim 15, wherein the PTA makes up 66% by weight of the combination of PTA, IPA, and MEG.

* * * * *